United States Patent
Okada (10) Patent No.: US 10,078,277 B2
(45) Date of Patent: Sep. 18, 2018

(54) ELECTROPHOTOGRAPHIC PHOTOSENSITIVE MEMBER (71) Applicant: KYOCERA Document Solutions Inc., Osaka (JP)

(72) Inventor: Hideki Okada, Osaka (JP)

(73) Assignee: KYOCERA Document Solutions Inc., Osaka (JP)

(*) Notice: Subject to any disclaimer, the term of this patent is extended or adjusted under 35 U.S.C. 154(b) by 0 days.

(21) Appl. No.: 15/827,830

(22) Filed: Nov. 30, 2017

(65) Prior Publication Data

US 2018/0157183 A1 Jun. 7, 2018

(30) Foreign Application Priority Data

Dec. 2, 2016 (JP) ................. 2016-234945

(51) Int. Cl.
G03G 5/06 (2006.01)
G03G 5/043 (2006.01)
G03G 5/047 (2006.01)
G03G 5/05 (2006.01)
C07C 211/58 (2006.01)
C07C 217/84 (2006.01)

(52) U.S. Cl.
CPC ............ G03G 5/065 (2013.01); C07C 211/58 (2013.01); C07C 217/84 (2013.01); G03G 5/043 (2013.01); G03G 5/047 (2013.01); G03G 5/0564 (2013.01); G03G 5/0567 (2013.01); G03G 5/0592 (2013.01); G03G 5/0614 (2013.01); G03G 5/0618 (2013.01); G03G 5/0633 (2013.01); G03G 5/0638 (2013.01)

(58) Field of Classification Search
CPC .. G03G 5/0631; G03G 5/0633; G03G 5/0638; G03G 5/0644; G03G 5/0646; G03G 5/065; G03G 5/0653; G03G 5/04; G03G 5/043; G03G 5/047; G03G 5/0609; G03G 5/0618
USPC ...... 430/58.15, 58.25, 58.5, 58.8, 77, 78, 83
See application file for complete search history.

(56) References Cited

U.S. PATENT DOCUMENTS 6,383,698 B1 5/2002 Okada et al.

FOREIGN PATENT DOCUMENTS

JP 2001-011074 A * 1/2001
JP 2001-222122 A 8/2001

OTHER PUBLICATIONS

Japanese Patent Office J-Plat-Pat machine-assisted English-language translation of JP 2001-011074 A (pub. Jan. 2001). (Year: 2001).*

* cited by examiner

Primary Examiner — Janis L Dote
(74) Attorney, Agent, or Firm — Studebaker & Brackett PC (57) ABSTRACT An electrophotographic photosensitive member includes a conductive substrate and a photosensitive layer containing a charge generating material, a hole transport material, a quinone derivative, and a binder resin. The quinone derivative is represented by general formula (1) or (2), where $R^1$, $R^2$, $R^3$, $R^4$, and $R^5$ each represent, independently of one another, a hydrogen atom, an alkyl group having a carbon number of at least 1 and no greater than 12, an aryl group that has a carbon number of at least 6 and no greater than 14 and that may have an alkyl group having a carbon number of at least 1 and no greater than 6, an aralkyl group having a carbon number of at least 7 and no greater than 12, or a cycloalkyl group having a carbon number of at least 3 and no greater than 10. Z represents an oxygen atom or a sulfur atom.

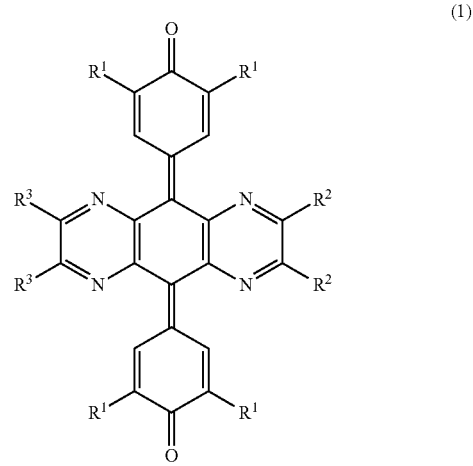

(1)

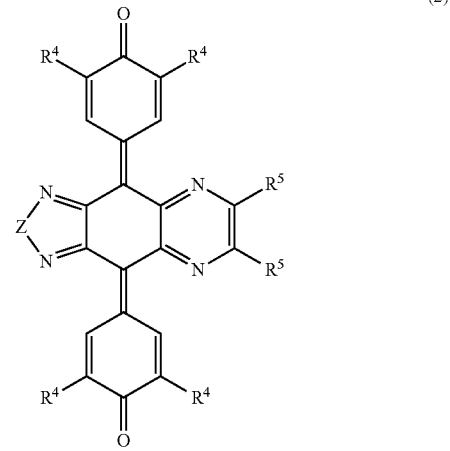

(2)

7 Claims, 2 Drawing Sheets

ELECTROPHOTOGRAPHIC PHOTOSENSITIVE MEMBER

INCORPORATION BY REFERENCE

The present application claims priority under 35 U.S.C. § 119 to Japanese Patent Application No. 2016-234945, filed on Dec. 2, 2016. The contents of this application are incorporated herein by reference in their entirety.

BACKGROUND

The present disclosure relates to an electrophotographic photosensitive member.

An electrophotographic photosensitive member is used in an electrophotographic image forming apparatus. The electrophotographic photosensitive member includes a photosensitive layer. As the electrophotographic photosensitive member, for example a multi-layer electrophotographic photosensitive member or a single-layer electrophotographic photosensitive member is used. The multi-layer electrophotographic photosensitive member includes as the photosensitive layer, a charge generating layer having a charge generating function and a charge transport layer having a charge transporting function. The single-layer electrophotographic photosensitive member includes as the photosensitive layer, a single-layer photosensitive layer having the charge generating function and the charge transporting function.

A known electrophotographic photosensitive member contains a compound represented by chemical formula (E-1) or (E-2).

SUMMARY

An electrophotographic photosensitive member of the present disclosure includes a conductive substrate and a photosensitive layer. The photosensitive layer contains a charge generating material, a hole transport material, a quinone derivative, and a binder resin. The quinone derivative is represented by general formula (1) or (2).

In the general formula (1), $R^1$, $R^2$, and $R^3$ each represent, independently of one another, a hydrogen atom, an alkyl group having a carbon number of at least 1 and no greater than 12, an aryl group having a carbon number of at least 6 and no greater than 14, an aralkyl group having a carbon number of at least 7 and no greater than 12, or a cycloalkyl group having a carbon number of at least 3 and no greater than 10. The aryl group having a carbon number of at least 6 and no greater than 14 may be substituted with an alkyl group having a carbon number of at least 1 and no greater than 6.

In the general formula (2), $R^4$ and $R^5$ each represent, independently of one another, a hydrogen atom, an alkyl group having a carbon number of at least 1 and no greater than 12, an aryl group having a carbon number of at least 6 and no greater than 14, an aralkyl group having a carbon number of at least 7 and no greater than 12, or a cycloalkyl group having a carbon number of at least 3 and no greater than 10. Z represents an oxygen atom or a sulfur atom. The aryl group having a carbon number of at least 6 and no greater than 14 may be substituted with an alkyl group having a carbon number of at least 1 and no greater than 6.

DETAILED DESCRIPTION

The following describes an embodiment of the present disclosure in detail. The present disclosure is by no means limited to the embodiment described below. The present disclosure is practicable with appropriate alterations within a scope of the object of the present disclosure. Note that some overlapping explanations may be omitted as appropriate, but such omission does not limit the gist of the present disclosure.

In the following description, the term "-based" may be appended to the name of a chemical compound in order to form a generic name encompassing both the chemical compound itself and derivatives thereof. Also, when the term "-based" is appended to the name of a chemical compound used in the name of a polymer, the term indicates that a repeating unit of the polymer originates from the chemical compound or a derivative thereof.

In the following description, an alkyl group having a carbon number of at least 1 and no greater than 12, an alkyl group having a carbon number of at least 1 and no greater than 6, an alkyl group having a carbon number of at least 1 and no greater than 4, an alkoxy group having a carbon number of at least 1 and no greater than 6, an aryl group having a carbon number of at least 6 and no greater than 14, an aralkyl group having a carbon number of at least 7 and no greater than 12, and a cycloalkyl group having a carbon number of at least 3 and no greater than 10 are as follows unless otherwise stated.

The alkyl group having a carbon number of at least 1 and no greater than 12 is an unsubstituted straight chain or branched chain alkyl group. Examples of the alkyl group having a carbon number of at least 1 and no greater than 12 include methyl group, ethyl group, n-propyl group, isopropyl group, n-butyl group, s-butyl group, t-butyl group, pentyl group, isopentyl group, neopentyl group, n-hexyl group, heptyl group, octyl group, nonyl group, decyl group, undecyl group, and dodecyl group.

The alkyl group having a carbon number of at least 1 and no greater than 6 is an unsubstituted straight chain or branched chain alkyl group. Examples of the alkyl group having a carbon number of at least 1 and no greater than 6 include methyl group, ethyl group, n-propyl group, isopropyl group, n-butyl group, s-butyl group, t-butyl group, pentyl group, isopentyl group, neopentyl group, and n-hexyl group.

The alkyl group having a carbon number of at least 1 and no greater than 4 is an unsubstituted straight chain or branched chain alkyl group. Examples of the alkyl group having a carbon number of at least 1 and no greater than 4 include methyl group, ethyl group, n-propyl group, isopropyl group, n-butyl group, s-butyl group, and t-butyl group.

The alkoxy group having a carbon number of at least 1 and no greater than 6 is an unsubstituted straight chain or branched chain alkoxy group. Examples of the alkoxy group having a carbon number of at least 1 and no greater than 6 include methoxy group, ethoxy group, n-propoxy group, isopropoxy group, n-butoxy group, s-butoxy group, t-butoxy group, pentoxy group, and hexyloxy group.

The aryl group having a carbon number of at least 6 and no greater than 14 is an unsubstituted aryl group. Examples of the aryl group having a carbon number of at least 6 and no greater than 14 include unsubstituted monocyclic aromatic hydrocarbon groups having a carbon number of at least 6 and no greater than 14, unsubstituted condensed bicyclic aromatic hydrocarbon groups having a carbon number of at least 6 and no greater than 14, and unsubstituted condensed tricyclic aromatic hydrocarbon groups having a carbon number of at least 6 and no greater than 14. Examples of the aryl group having a carbon number of at least 6 and no greater than 14 include phenyl group, naphthyl group, anthryl group, and phenanthryl group.

The aralkyl group having a carbon number of at least 7 and no greater than 12 is an unsubstituted straight chain or branched chain aralkyl group. Examples of the aralkyl group having a carbon number of at least 7 and no greater than 12 include: a group formed by bonding of a phenyl group to an alkyl group having a carbon number of 1 and no greater than 6; and a group formed by bonding of a naphthyl group to a methyl group or an ethyl group.

The cycloalkyl group having a carbon number of at least 3 and no greater than 10 is an unsubstituted cycloalkyl group. Examples of the cycloalkyl group having a carbon number of at least 3 and no greater than 10 include cyclopropyl group, cyclobutyl group, cyclopentyl group, cyclohexyl group, cycloheptyl group, cyclooctyl group, cyclononyl group, and cyclodecyl group.

<Electrophotographic Photosensitive Member>

An electrophotographic photosensitive member (hereinafter may be referred to as a photosensitive member) according to an embodiment of the present disclosure is excellent in sensitivity characteristics. The reason for this is presumed as follows. The photosensitive member according to the present embodiment includes a conductive substrate and a photosensitive layer. The photosensitive layer contains a charge generating material, a hole transport material, a quinone derivative, and a binder resin. The quinone derivative is represented by general formula (1) or (2). In the following description, the quinone derivative represented by general formula (1) may be referred to as a quinone derivative (1), and the quinone derivative represented by general formula (2) may be referred to as a quinone derivative (2). The quinone derivatives (1) and (2) have structure in which a heterocycle is fused with a central ring of p-terphenoquinone. The quinone derivatives (1) and (2) have a high degree of planeness and a π conjugated system. A spatial spread of the π conjugated system is relatively large. Therefore, a migration length of a carrier within molecules of the quinone derivatives (1) and (2) is relatively large, and a migration length of the carrier between the molecules is relatively small. Therefore, the quinone derivatives (1) and (2) are excellent in carrier acceptability and carrier transporting ability. It is thought that as a result, the photosensitive member according to the present embodiment is excellent in sensitivity characteristics.

Structure of the photosensitive member according to the present embodiment will be described. Examples of the photosensitive member include a single-layer electrophotographic photosensitive member (hereinafter may be referred to as a single-layer photosensitive member) and a multi-layer electrophotographic photosensitive member (hereinafter may be referred to as a multi-layer photosensitive member).

<1. Single-Layer Photosensitive Member>

Figure 1A:
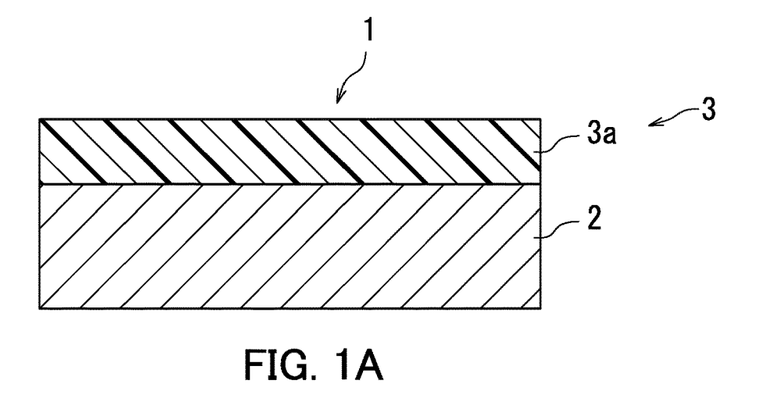
FIGS. 1A, 1B, and 1C are each a schematic cross-sectional view illustrating an example of an electrophotographic photosensitive member according to an embodiment of the present disclosure.
Figure 1B:
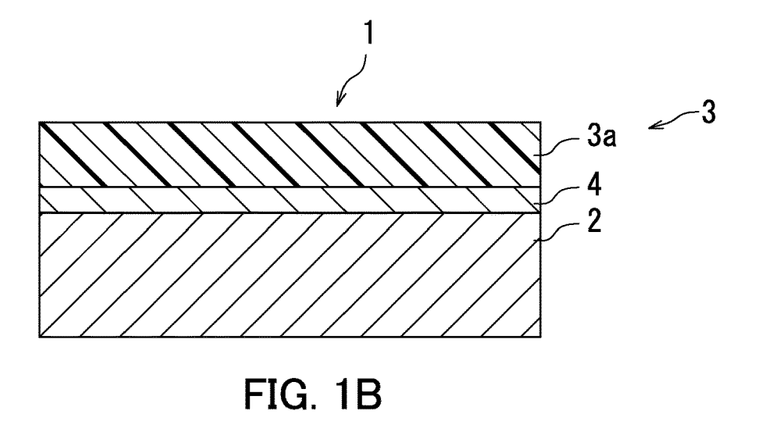
Figure 1C:
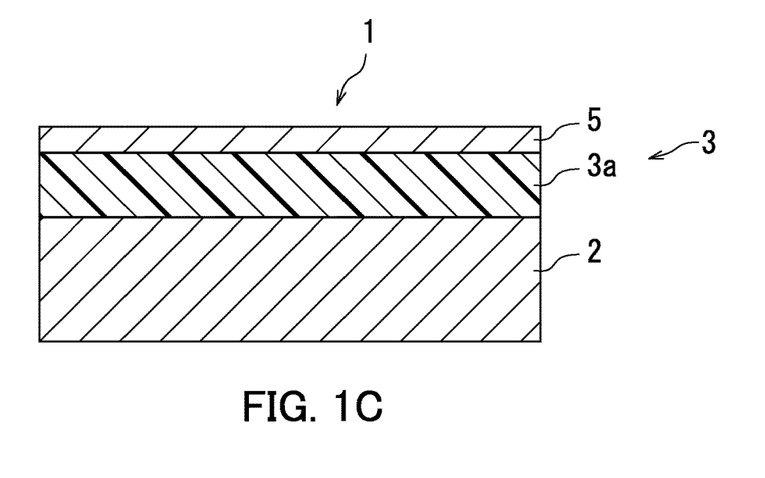

The following describes structure of a photosensitive member 1 in a configuration in which the photosensitive member is a single-layer photosensitive member with reference to FIGS. 1A to 1C. FIGS. 1A to 1C are schematic cross-sectional views illustrating the single-layer photosensitive member as an example of the photosensitive member according to the present embodiment.

As illustrated in FIG. 1A, the single-layer photosensitive member as the photosensitive member 1 includes a conductive substrate 2 and a photosensitive layer 3. The photosensitive layer 3 is a single-layer photosensitive layer 3a. The single-layer photosensitive layer 3a is the photosensitive layer 3 having single-layer structure.

As illustrated in FIG. 1B, the single-layer photosensitive member as the photosensitive member 1 may include the conductive substrate 2, the single-layer photosensitive layer 3a, and an intermediate layer (undercoat layer) 4. The intermediate layer 4 is provided between the conductive substrate 2 and the single-layer photosensitive layer 3a. Alternatively, as illustrated in FIG. 1C, a protective layer 5 may be provided on the single-layer photosensitive layer 3a.

The thickness of the single-layer photosensitive layer 3a is not particularly limited so long as the function of the single-layer photosensitive layer can be sufficiently achieved. The thickness of the single-layer photosensitive layer 3a is preferably at least 5 μm and no greater than 100 μm, and more preferably at least 10 μm and no greater than 50 μm.

The single-layer photosensitive layer 3a as the photosensitive layer 3 contains the charge generating material, the hole transport material, the quinone derivative (1) or (2) as an electron transport material, and the binder resin. The single-layer photosensitive layer 3a may contain various additives as necessary. That is, in a configuration in which the photosensitive member 1 is a single-layer photosensitive member, the charge generating material, the hole transport material, the quinone derivative (1) or (2) as the electron transport material, the binder resin, and components (for example, additives) added as necessary are contained in the photosensitive layer 3 (the single-layer photosensitive layer 3a) having the single-layer structure.

<2. Multi-layer Photosensitive Member>

Figure 2A:
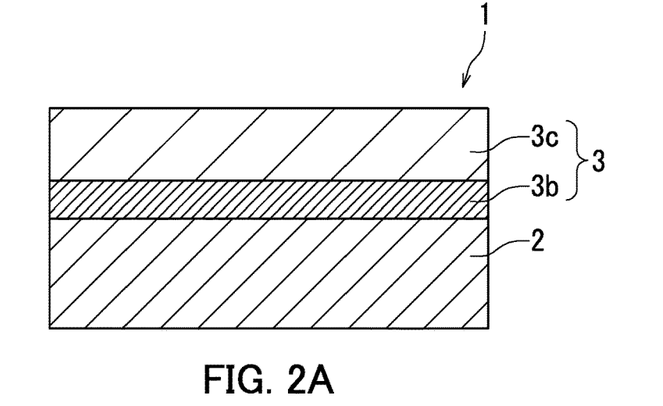
FIGS. 2A, 2B, and 2C are each a schematic cross-sectional view illustrating another example of the electrophotographic photosensitive member according to the embodiment of the present disclosure.
Figure 2B:
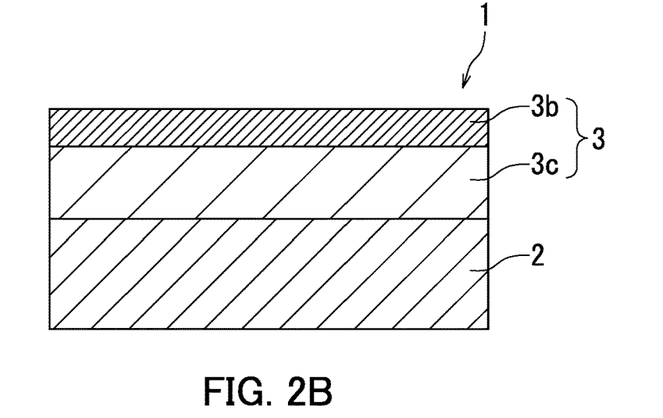
Figure 2C:
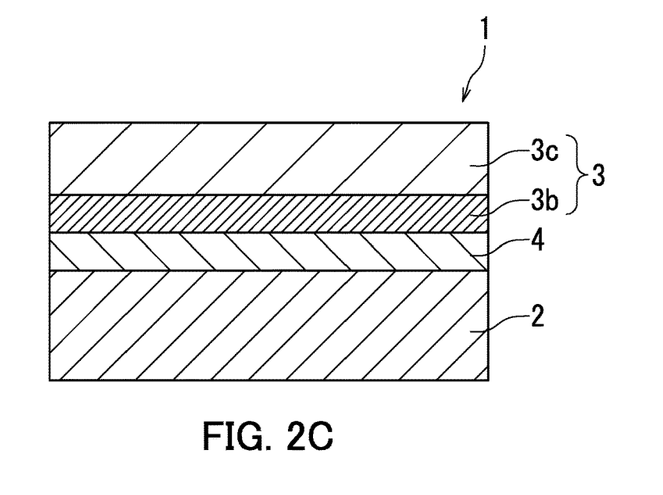

The following describes structure of the photosensitive member in a configuration in which the photosensitive member is a multi-layer photosensitive member with reference to FIGS. 2A to 2C. FIGS. 2A to 2C are schematic cross-sectional views illustrating the multi-layer photosensitive member as an example of the photosensitive member according to the present embodiment.

As illustrated in FIG. 2A, the multi-layer photosensitive member as the photosensitive member 1 includes the conductive substrate 2 and the photosensitive layer 3. The photosensitive layer 3 includes a charge generating layer 3b and a charge transport layer 3c. In order to improve abrasion resistance of the multi-layer photosensitive member, it is preferable that the charge generating layer 3b is located on the conductive substrate 2 and the charge transport layer 3c is located on the charge generating layer 3b as illustrated in FIG. 2A.

Alternatively, in the multi-layer photosensitive member as the photosensitive member 1, the charge transport layer 3c may be located on the conductive substrate 2 and the charge generating layer 3b may be located on the charge transport layer 3c as illustrated in FIG. 2B.

As illustrated in FIG. 2C, the multi-layer photosensitive member as the photosensitive member 1 may include the conductive substrate 2, the photosensitive layer 3, and the intermediate layer (the undercoat layer) 4. The intermediate layer 4 is provided between the conductive substrate 2 and the photosensitive layer 3. Also, the protective layer 5 (see FIG. 1C) may be provided on the photosensitive layer 3.

The thicknesses of the charge generating layer 3b and the charge transport layer 3c are not particularly limited so long as functions of the respective layers can be sufficiently achieved. The thickness of the charge generating layer 3b is preferably at least 0.01 μm and no greater than 5 μm, and more preferably at least 0.1 μm and no greater than 3 μm. The thickness of the charge transport layer 3c is preferably at least 2 μm and no greater than 100 μm, and more preferably at least 5 μm and no greater than 50 μm.

The charge generating layer 3b in the photosensitive layer 3 contains for example the charge generating material and a binder resin (hereinafter may be referred to as a base resin) of the charge generating layer. The charge generating layer 3b may contain various additives as necessary.

The charge transport layer 3c contains for example the hole transport material, the quinone derivative (1) or (2) as an electron acceptor compound, and the binder resin. The charge transport layer 3c may contain various additives as necessary.

Next, components of the multi-layer photosensitive member and the single-layer photosensitive member will be described.

<3. Conductive Substrate>

The conductive substrate 2 is not particularly limited so long as the conductive substrate 2 can be used in the photosensitive member 1. It is only required that at least a surface portion of the conductive substrate 2 is formed from a material (hereinafter may be referred to as a conductive material) having electrical conductivity. Examples of the conductive substrate 2 include a conductive substrate formed from the conductive material or a conductive substrate coated with the conductive material. Examples of the conductive material include aluminum, iron, copper, tin, platinum, silver, vanadium, molybdenum, chromium, cadmium, titanium, nickel, palladium, and indium. One of the above-listed conductive materials may be used alone, or two or more of the above-listed conductive materials may be used in combination. Examples of the combination of two or more conductive materials include alloys (specific examples include aluminum alloys, stainless steel, and brass). Among the above-listed conductive materials, aluminum and aluminum alloys are preferable in terms of good charge mobility from the photosensitive layer 3 to the conductive substrate 2.

The shape of the conductive substrate 2 is selected as appropriate in accordance with structure of an image forming apparatus. Examples of the shape of the conductive substrate 2 include a sheet-like shape and a drum-like shape. Also, the thickness of the conductive substrate 2 is selected as appropriate in accordance with the shape of the conductive substrate 2.

<4. Electron Transport Material and Electron Acceptor Compound>

As described above, in a configuration in which the photosensitive member 1 is a multi-layer photosensitive member, the charge transport layer 3c contains the quinone derivative (1) or (2) as the electron acceptor compound. In a configuration in which the photosensitive member 1 is a single-layer photosensitive member, the single-layer photosensitive layer 3a contains the quinone derivative (1) or (2) as the electron transport material.

The quinone derivatives (1) and (2) are represented by general formulas (1) and (2) respectively.

(1)

(2)

In general formula (1), R¹, R², and R³ each represent, independently of one another, a hydrogen atom, an alkyl group having a carbon number of at least 1 and no greater than 12, an aryl group having a carbon number of at least 6 and no greater than 14, an aralkyl group having a carbon number of at least 7 and no greater than 12, or a cycloalkyl group having a carbon number of at least 3 and no greater than 10. The aryl group having a carbon number of at least 6 and no greater than 14 may be substituted with an alkyl group having a carbon number of at least 1 and no greater than 6.

In general formula (2), R⁴ and R⁵ each represent, independently of one another, a hydrogen atom, an alkyl group having a carbon number of at least 1 and no greater than 12, an aryl group having a carbon number of at least 6 and no greater than 14, an aralkyl group having a carbon number of at least 7 and no greater than 12, or a cycloalkyl group having a carbon number of at least 3 and no greater than 10. Z represents an oxygen atom or a sulfur atom. The aryl group having a carbon number of at least 6 and no greater than 14 may be substituted with an alkyl group having a carbon number of at least 1 and no greater than 6.

The alkyl group which has a carbon number of at least 1 and no greater than 12 and which is represented by R¹, R², and R³ in general formula (1) is preferably an alkyl group having a carbon number of at least 1 and no greater than 6, more preferably an alkyl group having a carbon number of at least 1 and no greater than 4, further preferably a butyl group, and particularly preferably an n-butyl group or a t-butyl group.

The aryl group which has a carbon number of at least 6 and no greater than 14 and which is represented by R¹, R², and R³ in general formula (1) is preferably a phenyl group. The aryl group having a carbon number of at least 6 and no greater than 14 may have an alkyl group having a carbon number of at least 1 and no greater than 6 as a substituent. The alkyl group having a carbon number of at least 1 and no greater than 6 as the substituent is preferably an alkyl group having a carbon number of at least 1 and no greater than 3, and more preferably a methyl group. The aryl group which has a carbon number of at least 6 and no greater than 14 and which may be substituted with the alkyl group having a carbon number of at least 1 and no greater than 6 is preferably a phenyl group substituted with an alkyl group having a carbon number of at least 1 and no greater than 3, more preferably a methylphenyl group, and further preferably a p-methylphenyl group.

In general formula (1), R¹, R², and R³ each represent, independently of one another, preferably an alkyl group having a carbon number of at least 1 and no greater than 12 or an aryl group which has a carbon number of at least 6 and no greater than 14 and which is substituted with an alkyl group having a carbon number of at least 1 and no greater than 6, more preferably an alkyl group having a carbon number of at least 1 and no greater than 4 or a phenyl group substituted with an alkyl group having a carbon number of at least 1 and no greater than 3, further preferably a butyl group or a methylphenyl group, and particularly preferably an n-butyl group, a t-butyl group, or a p-methylphenyl group.

In general formula (1), the chemical groups R¹ may be the same or different from one another. The chemical groups R² may be the same or different from one another. The chemical groups R³ may be the same or different from one another.

In order to further improve sensitivity characteristics of the photosensitive member 1, R² and R³ in general formula (1) each preferably represent, independently of one another, an aryl group which has a carbon number of at least 6 and no greater than 14 and which may be substituted with an alkyl group having a carbon number of at least 1 and no greater than 6, an aralkyl group having a carbon number of at least 7 and no greater than 12, an alkyl group having a carbon number of at least 1 and no greater than 12, or a cycloalkyl group having a carbon number of at least 3 and no greater than 10. In the above configuration, the quinone derivative (1) has a substituent other than a hydrogen atom in the heterocycle fused with the central ring. Therefore, the quinone derivative (1) has improved solubility in a solvent of an application liquid for photosensitive layer formation and improved compatibility with the binder resin. Also, crystallization of the quinone derivative (1) in the photosensitive layer 3 is inhibited, and the quinone derivative (1) tends to be dispersed in the photosensitive layer 3.

Specific examples of the quinone derivative (1) include a quinone derivative represented by chemical formula (1-1) (hereinafter may be referred to as a quinone derivative (1-1)) and a quinone derivative represented by chemical formula (1-2) (hereinafter may be referred to as a quinone derivative (1-2)).

(1-1)

(1-2)

Among the above quinone derivatives (1), the quinone derivative (1-2) is preferable.

In general formula (2), the alkyl group which has a carbon number of at least 1 and no greater than 12 and which is represented by $R^4$ and $R^5$ is preferably an alkyl group having a carbon number of at least 1 and no greater than 6, more preferably an alkyl group having a carbon number of at least 1 and no greater than 4, further preferably a butyl group, and particularly preferably an n-butyl group or a t-butyl group.

In general formula (2), the aryl group which has a carbon number of at least 6 and no greater than 14 and which is represented by $R^4$ and $R^5$ is preferably a phenyl group. The aryl group having a carbon number of at least 6 and no greater than 14 may have an alkyl group having a carbon number of at least 1 and no greater than 6 as a substituent. The alkyl group having a carbon number of at least 1 and no greater than 6 as the substituent is preferably an alkyl group having a carbon number of at least 1 and no greater than 3, and more preferably a methyl group. The aryl group which has a carbon number of at least 6 and no greater than 14 and which may be substituted with the alkyl group having a carbon number of at least 1 and no greater than 6 is preferably a phenyl group substituted with an alkyl group having carbon number of at least 1 and no greater than 3, more preferably a methylphenyl group, and further preferably a p-methylphenyl group.

In general formula (2), $R^4$ and $R^5$ each represent, independently of one another, preferably an alkyl group having a carbon number of at least 1 and no greater than 12 or an aryl group which has a carbon number of at least 6 and no greater than 14 and which is substituted with an alkyl group having a carbon number of at least 1 and no greater than 6, more preferably an alkyl group having a carbon number of at least 1 and no greater than 4 or a phenyl group substituted with an alkyl group having a carbon number of at least 1 and no greater than 3, further preferably a butyl group or a methylphenyl group, and particularly preferably an n-butyl group, a t-butyl group, or a p-methylphenyl group.

In general formula (2), the chemical groups $R^4$ may be the same or different from one another. The chemical groups $R^5$ may be the same or different from one another.

In order to further improve sensitivity characteristics of the photosensitive member 1, $R^5$ in general formula (2) preferably represents, independently of one another, an aryl group which has a carbon number of at least 6 and no greater than 14 and which may be substituted with an alkyl group having a carbon number of at least 1 and no greater than 6, an aralkyl group having a carbon number of at least 7 and no greater than 12, an alkyl group having a carbon number of at least 1 and no greater than 12, or a cycloalkyl group having a carbon number of at least 3 and no greater than 10. In the above configuration, the quinone derivative (2) has a substituent other than a hydrogen atom in the heterocycle fused with the central ring. Therefore, the quinone derivative (2) has improved solubility in the solvent of the application liquid for photosensitive layer formation and improved compatibility with the binder resin. Also, crystallization of the quinone derivative (2) in the photosensitive layer 3 is inhibited, and the quinone derivative (2) tends to be dispersed in the photosensitive layer 3.

Specific examples of the quinone derivative (2) include a quinone derivative represented by chemical formula (2-1) (hereinafter may be referred to as a quinone derivative (2-1)) and a quinone derivative represented by chemical formula (2-2) (hereinafter may be referred to as a quinone derivative (2-2)).

(2-1)

-continued (2-2)

Among the above quinone derivatives (2), the quinone derivative (2-2) is preferable.

In a configuration in which the photosensitive member 1 is a multi-layer photosensitive member, the amount of the quinone derivative (1) or (2) is preferably at least 10 parts by mass and no greater than 200 parts by mass relative to 100 parts by mass of the binder resin contained in the charge transport layer 3c, and more preferably at least 20 parts by mass and no greater than 100 parts by mass.

<Method for Producing Quinone Derivative>

(Method for Producing Quinone Derivative (1))

The quinone derivative (1) is produced for example through reaction (hereinafter may be referred to as reaction (R-1)) represented by reaction formula (R-1) or by a method in accordance with the reaction formula (R-1). A method for producing the quinone derivative (1) includes the reaction (R-1) for example.

In the reaction (R-1), $R^1$, $R^2$, and $R^3$ in general formula (A1) are the same as $R^1$, $R^2$, and $R^3$ in general formula (1), respectively.

-continued

In the reaction (R-1), 1 equivalent of a phenol derivative (hereinafter may be referred to as a phenol derivative (A1)) represented by general formula (A1) is caused to react in a solvent in the presence of an oxidant to yield 1 equivalent of the quinone derivative (1). In the reaction (R-1), at least 3 mol and no greater than 40 mol of the oxidant is preferably added relative to 1 mol of the phenol derivative (A1). When the oxidant is added in an amount of at least 3 mol relative to 1 mol of the phenol derivative (A1), the yield of the quinone derivative (1) can be easily improved. When the oxidant is added in an amount of no greater than 40 mol relative to 1 mol of the phenol derivative (A1), the oxidant is prevented from being left unreacted after the reaction, and the quinone derivative (1) can be purified easily. A reaction time of the reaction (R-1) is preferably at least 5 hours and no longer than 30 hours. A reaction temperature of the reaction (R-1) is preferably at least 10° C. and no greater than 50° C. Examples of the solvent include chloroform and dichloromethane. Examples of the oxidant include potassium permanganate, hydrogen peroxide, meta-chloroperbenzoic acid, and peroxyacetic acid.

Production of the quinone derivative (1) may include other processes as necessary. Examples of the other processes include a purification process. Examples of purification methods include known methods (specific examples include filtration, chromatography, and crystallization).

(Method for Producing Quinone Derivative (2))

The quinone derivative (2) is produced for example through reaction (hereinafter may be referred to as reaction (R-2)) represented by reaction formula (R-2) or a method in accordance with the reaction formula (R-2). A method for producing the quinone derivative (2) includes the reaction (R-2) for example.

In the reaction (R-2), $R^4$ and $R^5$ in general formula (A2) are the same as $R^4$ and $R^5$ in general formula (2), respectively.

(A2)

(2)

In the reaction (R-2), 1 equivalent of a phenol derivative (hereinafter may be referred to as a phenol derivative (A2)) represented by general formula (A2) is caused to react in a solvent in the presence of an oxidant to yield 1 equivalent of the quinone derivative (2). In the reaction (R-2), at least 3 mol and no greater than 40 mol of the oxidant is preferably added relative to 1 mol of the phenol derivative (A2). When the oxidant is added in an amount of at least 3 mol relative to 1 mol of the phenol derivative (A2), the yield of the quinone derivative (2) can be easily improved. When the oxidant is added in an amount of no greater than 40 mol relative to 1 mol of the phenol derivative (A2), the oxidant is prevented from being left unreacted after the reaction, and the quinone derivative (2) can be purified easily. A reaction time of the reaction (R-2) is preferably at least 5 hours and no longer than 30 hours. A reaction temperature of the reaction (R-2) is preferably at least 10° C. and no greater than 50° C. Examples of the solvent include chloroform and dichloromethane. Examples of the oxidant include potassium permanganate, hydrogen peroxide, meta-chloroperbenzoic acid, and peroxyacetic acid.

Production of the quinone derivative (2) may include other processes as necessary. Examples of the other processes include a purification process. Examples of purification methods include known methods (specific examples include filtration, chromatography, and crystallization).

In a configuration in which the photosensitive member is a single-layer photosensitive member, the amount of the quinone derivative (1) or (2) is preferably at least 10 parts by mass and no greater than 200 parts by mass relative to 100 parts by mass of the binder resin contained in the single-layer photosensitive layer, more preferably at least 10 parts by mass and no greater than 100 parts by mass, and particularly preferably at least 10 parts by mass and no greater than 75 parts by mass.

The charge transport layer 3c may further contain another electron acceptor compound in addition to the quinone derivative (1) or (2). The single-layer photosensitive layer 3a may further contain another electron transport material in addition to the quinone derivative (1) or (2). Examples of the other electron acceptor compound and the other electron transport material include quinone-based compounds other than the quinone derivatives (1) and (2), diimide-based compounds, hydrazone-based compounds, malononitrile-based compounds, thiopyran-based compounds, trinitrothioxanthone-based compounds, 3,4,5,7-tetranitro-9-fluorenone-based compounds, dinitroanthracene-based compounds, dinitroacridine-based compounds, tetracyanoethylene, 2,4,8-trinitrothioxanthone, dinitrobenzene, dinitroacridine, succinic anhydride, maleic anhydride, and dibromomaleic anhydride. Examples of the quinone-based compounds include diphenoquinone-based compounds, azoquinone-based compounds, anthraquinone-based compounds, naphthoquinone-based compounds, nitroanthraquinone-based compounds, and dinitroanthraquinone-based compounds. One of the above-listed electron acceptor compounds and electron transport materials may be used alone, or two or more of the above-listed electron acceptor compounds and electron transport materials may be used in combination.

<5. Hole Transport Material>

Examples of the hole transport material include diamine derivatives (specific examples include benzidine derivatives, N,N,N',N'-tetraphenylphenylenediamine derivatives, N,N,N',N'-tetraphenylnaphtylenediamine derivatives, and N,N,N',N'-tetraphenylphenanthrylenediamine derivatives), oxadiazole-based compounds (specific examples include 2,5-di(4-methylaminophenyl)-1,3,4-oxadiazole), styryl compounds (specific examples include 9-(4-diethylaminostyryl)anthracene), carbazole compounds (specific examples include polyvinyl carbazole), organic polysilane compounds, pyrazoline-based compounds (specific examples include 1-phenyl-3-(p-dimethylaminophenyl)pyrazoline), hydrazone-based compounds, indole-based compounds, oxazole-based compounds, isoxazole-based compounds, thiazole-based compounds, thiadiazole-based compounds, imidazole-based compounds, pyrazole-based compounds, and triazole-based compounds. One of the above-listed hole transport materials may be used alone, or two or more of the above-listed hole transport materials may be used in combination. Among the above-listed hole transport materials, a compound (benzidine derivative) represented by general formula (3) is preferable.

(3)

In general formula (3), $R^{21}$, $R^{22}$, $R^{23}$, $R^{24}$, $R^{25}$, and $R^{26}$ each represent, independently of one another, an alkyl group having a carbon number of at least 1 and no greater than 6 or an alkoxy group having a carbon number of at least 1 and no greater than 6. Also, p, q, v, and w each represent, independently of one another, an integer from 0 to 5. Also, m and n each represent, independently of one another, an integer from 0 to 4.

In general formula (3), $R^{21}$, $R^{22}$, $R^{23}$, $R^{24}$, $R^{25}$, and $R^{26}$ each represent preferably an alkyl group having a carbon number of at least 1 and no greater than 6, more preferably an alkyl group having a carbon number of at least 1 and no greater than 3, and further preferably a methyl group. Also, p, q, v, w, m, and n each represent preferably 1.

The compound represented by general formula (3) is preferably a compound (hereinafter may be referred to as a hole transport material (H-1)) represented by chemical formula (H-1).

(H-1)

In a configuration in which the photosensitive member 1 is a multi-layer photosensitive member, the amount of the hole transport material is preferably at least 10 parts by mass and no greater than 200 parts by mass relative to 100 parts by mass of the binder resin contained in the charge transport layer 3c, and more preferably at least 20 parts by mass and no greater than 100 parts by mass.

In a configuration in which the photosensitive member 1 is a single-layer photosensitive member, the amount of the hole transport material is preferably at least 10 parts by mass and no greater than 200 parts by mass relative to 100 parts by mass of the binder resin contained in the single-layer photosensitive layer 3a, more preferably at least 10 parts by mass and no greater than 100 parts by mass, and particularly preferably at least 10 parts by mass and no greater than 90 parts by mass.

<6. Charge Generating Material>

The charge generating material is not particularly limited so long as the charge generating material can be used in the photosensitive member 1. Examples of the charge generating material include phthalocyanine-based pigments, perylene-based pigments, bisazo pigments, tris-azo pigments, dithioketopyrrolopyrrole pigments, metal-free naphthalocyanine pigments, metal naphthalocyanine pigments, squaraine pigments, indigo pigments, azulenium pigments, cyanine pigments, powders of inorganic photoconductive materials (specific examples include selenium, selenium-tellurium, selenium-arsenic, cadmium sulfide, and amorphous silicon), pyrylium pigments, anthanthrone-based pigments, triphenylmethane-based pigments, threne-based pigments, toluidine-based pigments, pyrazoline-based pigments, and quinacridone-based pigments. One charge generating material may be used alone, or two or more charge generating materials may be used in combination.

Examples of the phthalocyanine-based pigments include a metal-free phthalocyanine pigment (hereinafter may be referred to as a compound (C-1)) represented by chemical formula (C-1) and metal phthalocyanine pigments. Examples of the metal phthalocyanine pigments include a titanyl phthalocyanine pigment (hereinafter may be referred to as a compound (C-2)) represented by chemical formula (C-2), hydroxygallium phthalocyanine pigments, and chlorogallium phthalocyanine pigments. The phthalocyanine-based pigments may be crystalline or non-crystalline. Crystal structure (for example, α-form, β-form, Y-form, V-form, or II-form) of the phthalocyanine-based pigments is not particularly limited. The phthalocyanine-based pigments having various crystal structures may be used.

(C-1)

(C-2)

Examples of crystalline metal-free phthalocyanine pigments include a metal-free phthalocyanine pigment (hereinafter may be referred to as X-form crystalline metal-free phthalocyanine) having an X-form crystal structure. Examples of crystalline titanyl phthalocyanine pigments include titanyl phthalocyanine pigments (hereinafter referred to as α-form, β-form, and Y-form crystalline titanyl phthalocyanines) having α-form, β-form, and Y-form crystal structures. Examples of crystalline hydroxygallium phthalocyanine pigments include a hydroxygallium phthalocyanine pigment having a V-form crystal structure. Examples of crystalline chlorogallium phthalocyanine pigments include a chlorogallium phthalocyanine pigment having a II-form crystal structure.

For image forming apparatuses employing, for example, a digital optical system, a photosensitive member having sensitivity in a wavelength range of 700 nm or longer is preferred. Examples of such image forming apparatuses include a laser printer or a facsimile machine that includes a semiconductor laser. As the charge generating material, phthalocyanine-based pigments are preferable, and metal-free phthalocyanine pigments and titanyl phthalocyanine pigments are more preferable in terms of their high quantum yield in the wavelength range of 700 nm or longer. In a configuration in which the photosensitive layer 3 contains the quinone derivative (1) or (2), an X-form metal-free phthalocyanine pigment and an Y-form titanyl phthalocyanine pigment are further preferable as the charge generating material in order to further improve electrical characteristics of the photosensitive member.

The Y-form titanyl phthalocyanine pigment exhibits a main peak, for example, at a Bragg angle (2θ±0.2°) of 27.2° in a CuKα characteristic X-ray diffraction spectrum. The term main peak in the CuKα characteristic X-ray diffraction spectrum refers to a most intense or second most intense peak within a range of Bragg angles (2θ±0.2°) from 3° to 40°.

(Method for Measuring CuKα Characteristic X-Ray Diffraction Spectrum)

An example of methods for measuring the CuKα characteristic X-ray diffraction spectrum will be described. A sample (titanyl phthalocyanine) is loaded into a sample holder of an X-ray diffraction spectrometer (for example, "RINT (registered Japanese trademark) 1100" manufactured by Rigaku Corporation) to measure the X-ray diffraction spectrum. Measurement conditions are as follows: a Cu X-ray tube; a tube voltage of 40 kV; a tube current of 30 mA; and X-rays characteristic of CuKα having a wavelength of 1.542 Å. The measurement range (2θ) is from 3° to 40° (start angle: 3°, stop angle: 40°) and the scanning speed is 10°/minute.

For the photosensitive member included in image forming apparatuses including a short-wavelength laser light source, anthanthrone-based pigments are preferably used as the charge generating material. The wavelength of the short-wavelength laser light is for example at least 350 nm and no greater than 550 nm. In a configuration in which the photosensitive member 1 is a multi-layer photosensitive member, the amount of the charge generating material is preferably at least 5 parts by mass and no greater than 1000 parts by mass relative to 100 parts by mass of the base resin contained in the charge generating layer 3b, and more preferably at least 30 parts by mass and no greater than 500 parts by mass.

In a configuration in which the photosensitive member 1 is a single-layer photosensitive member, the amount of the charge generating material is preferably at least 0.1 parts by mass and no greater than 50 parts by mass relative to 100 parts by mass of the binder resin contained in the single-layer photosensitive layer 3a, more preferably at least 0.5 parts by mass and no greater than 30 parts by mass, and particularly preferably at least 0.5 parts by mass and no greater than 6.0 parts by mass.

<7. Binder Resin>

Examples of the binder resin include thermoplastic resins, thermosetting resins, and photocurable resins. Examples of the thermoplastic resins include polycarbonate resins, polyarylate resins, styrene-butadiene-based resins, styrene-acrylonitrile resins, styrene-maleic acid resins, acrylic acid-based resins, styrene-acrylic acid-based resins, polyethylene resins, ethylene-vinyl acetate resins, chlorinated polyethylene resins, polyvinyl chloride resins, polypropylene resins, ionomer resins, vinyl chloride-vinyl acetate resins, alkyd resins, polyamide resins, urethane resins, polysulfone resins, diallyl phthalate resins, ketone resins, polyvinyl butyral resins, polyester resins, and polyether resins. Examples of the thermosetting resins include silicone resins, epoxy resins, phenolic resins, urea resins, and melamine resins. Examples of the photocurable resins include epoxy-acrylic acid-based resins (specific examples include acrylic acid derivative adducts of epoxy compounds) and urethane-acrylic acid-based resins (specific examples include acrylic acid derivative adducts of urethane compounds). One of the above-listed binder resins may be used alone, or two or more of the above-listed binder resins may be used in combination.

Among the above-listed resins, polycarbonate resins are preferable for obtaining the single-layer photosensitive layer 3a and the charge transport layer 3c having excellent balance in terms of processability, mechanical strength, optical properties, and abrasion resistance. Examples of the polycarbonate resins include a bisphenol Z polycarbonate resin (hereinafter may be referred to as a polycarbonate resin (Resin-1)) that has a repeating unit represented by the following chemical formula (Resin-1), a bisphenol ZC polycarbonate resin, a bisphenol C polycarbonate resin, and a bisphenol A polycarbonate resin.

(Resin-1)

The binder resin preferably has a viscosity average molecular weight of at least 40,000, and more preferably at least 40,000 and no greater than 52,500. In a configuration in which the viscosity average molecular weight of the binder resin is at least 40,000, abrasion resistance of the photosensitive member 1 can be improved easily. In a configuration in which the viscosity average molecular weight of the binder resin is no greater than 52,500, the binder resin easily dissolves in a solvent in formation of the photosensitive layer 3, and viscosity of an application liquid for charge transport layer formation or an application liquid for single-layer photosensitive layer formation does not become excessively high. As a result, the charge transport layer 3c or the single-layer photosensitive layer 3a can be formed easily.

<8. Base Resin>

In a configuration in which the photosensitive member 1 is a multi-layer photosensitive member, the charge generating layer 3b may contain the base resin. The base resin is not particularly limited so long as the base resin can be used in the photosensitive member 1. Examples of the base resin include thermoplastic resins, thermosetting resins, and photocurable resins. Examples of the thermoplastic resins include styrene-butadiene resins, styrene-acrylonitrile resins, styrene-maleic acid resins, styrene-acrylic acid-based resins, acrylic acid-based resins, polyethylene resins, ethylene-vinyl acetate resins, chlorinated polyethylene resins, polyvinyl chloride resins, polypropylene resins, ionomers, vinyl chloride-vinyl acetate resins, alkyd resins, polyamide resins, urethane resins, polycarbonate resins, polyarylate resins, polysulfone resins, diallyl phthalate resins, ketone resins, polyvinyl butyral resins, polyether resins, and polyester resins. Examples of the thermosetting resins include silicone resins, epoxy resins, phenolic resins, urea resins, melamine resins, and other crosslinkable thermosetting resins. Examples of the photocurable resins include epoxy-acrylic acid-based resins (specific examples include acrylic acid derivative adducts of epoxy compounds) and urethane-acrylic acid-based resins (specific examples include acrylic acid derivative adducts of urethane compounds). One base resin may be used alone, or two or more base resins may be used in combination.

A multi-layer photosensitive member is typically produced by forming the charge generating layer 3b on the conductive substrate and forming the charge transport layer 3c on the charge generating layer 3b. In the formation of the charge transport layer 3c, the application liquid for charge transport layer formation is applied on the charge generating layer 3b. In order to prevent dissolution of the charge generating layer 3b in a solvent of the application liquid for charge transport layer formation, it is preferable that the base resin contained in the charge generating layer 3b differs from the binder resin contained in the charge transport layer 3c.

<9. Additive>

The photosensitive layer 3 (the charge generating layer 3b, the charge transport layer 3c, or the single-layer photosensitive layer 3a) of the photosensitive member may contain various additives as necessary. Examples of the additives include antidegradants (specific examples include an antioxidant, a radical scavenger, a quencher, and an ultraviolet absorbing agent), a softener, a surface modifier, an extender, a thickener, a dispersion stabilizer, a wax, a donor, a surfactant, a plasticizer, a sensitizer, and a leveling agent.

<10. Intermediate Layer>

The intermediate layer (undercoat layer) 4 contains for example inorganic particles and a resin (a resin for the intermediate layer). It is thought that in a configuration in which the intermediate layer 4 is provided, flow of electric current generated when the photosensitive member 1 is exposed to light is facilitated and an increase in resistance is inhibited, while insulation is maintained at a degree sufficient to inhibit occurrence of leakage current.

Examples of the inorganic particles include particles of metals (specific examples include aluminum, iron, and copper), particles of metal oxides (specific examples include titanium oxide, alumina, zirconium oxide, tin oxide, and zinc oxide), and particles of non-metal oxides (specific examples include silica). One type of the above-listed inorganic particles may be used alone, or two or more types of the above-listed inorganic particles may be used in combination.

The resin for the intermediate layer is not particularly limited so long as the resin can be used for forming the intermediate layer 4. The intermediate layer 4 may contain various additives. The additives are the same as the additives of the photosensitive layer 3.

<11. Method for Producing Photosensitive Member>

In a configuration in which the photosensitive member 1 is a multi-layer photosensitive member, the multi-layer photosensitive member is produced as follows, for example. First, the application liquid for charge generating layer formation and the application liquid for charge transport layer formation are prepared. The application liquid for charge generating layer formation is applied on the conductive substrate 2 to form an applied film. The applied film is dried to form the charge generating layer 3b. Subsequently, the application liquid for charge transport layer formation is applied on the charge generating layer 3b to form an applied film. The applied film is dried to form the charge transport layer 3c. Through the above, the multi-layer photosensitive member is produced.

The application liquid for charge generating layer formation is prepared by dissolving or dispersing the charge generating material and components (for example, the base resin and various additives) added as necessary in a solvent. The application liquid for charge transport layer formation is prepared by dissolving or dispersing the quinone derivative (1) or (2) as the electron acceptor compound, the binder resin, the hole transport material, and components (for example, additives) added as necessary in a solvent.

In a configuration in which the photosensitive member 1 is a single-layer photosensitive member, the single-layer photosensitive member is produced by applying the application liquid for single-layer photosensitive layer formation on the conductive substrate to form an applied film, and drying the applied film. The application liquid for single-layer photosensitive layer formation is prepared by dissolving or dispersing the charge generating material, the hole transport material, the quinone derivative (1) or (2) as the electron transport material, the binder resin, and components (for example, additives) added as necessary in a solvent.

The solvent contained in the application liquid for charge generating layer formation, the application liquid for charge transport layer formation, or the application liquid for single-layer photosensitive layer formation (hereinafter, each of these application liquids may be referred to as an application liquid) is not particularly limited so long as the components contained in the application liquid can be dissolved or dispersed in the solvent, and the solvent can be removed from the applied film. Examples of the solvent include alcohols (specific examples include methanol, ethanol, isopropanol, and butanol), aliphatic hydrocarbons (specific examples include n-hexane, octane, and cyclohexane), aromatic hydrocarbons (specific examples include benzene, toluene, and xylene), halogenated hydrocarbons (specific examples include dichloromethane, dichloroethane, carbon tetrachloride, and chlorobenzene), ethers (specific examples include dimethyl ether, diethyl ether, tetrahydrofuran, ethylene glycol dimethyl ether, diethylene glycol dimethyl ether, and propylene glycol monomethyl ether), ketones (specific examples include acetone, methyl ethyl ketone, and cyclohexanone), esters (specific examples include ethyl acetate and methyl acetate), dimethyl formaldehyde, dimethyl formamide, and dimethyl sulfoxide. One of the above-listed solvents is used alone, or two or more of the above-listed solvents are used in combination. In order to improve workability during production of the photosensitive member 1, a non-halogenated solvent (i.e., a solvent other than halogenated hydrocarbons) is preferably used as the solvent.

The application liquid is prepared by mixing and dispersing the components in the solvent. The mixing and dispersing can be performed using for example a bead mill, a roll mill, a ball mill, an attritor, a paint shaker, or an ultrasonic disperser.

In order to improve dispersibility of the components, for example a surfactant may be contained in the application liquid.

A method for applying the application liquid is not particularly limited so long as the application liquid can be applied uniformly on the conductive substrate. Examples of the method for applying the application liquid include dip coating, spray coating, spin coating, and bar coating.

A method for drying the applied film is not particularly limited so long as the solvent in the application liquid can be evaporated. Examples of the method for drying the applied film include thermal treatment (hot-air drying) using a high-temperature dryer or a reduced pressure dryer. The thermal treatment is preferably performed for example at a temperature not lower than 40° C. and not higher than 150° C. for a time not shorter than 3 minutes and not longer than 120 minutes.

Note that the method for producing the photosensitive member 1 may further include either or both of a process for forming the intermediate layer 4 and a process for forming the protective layer 5, as necessary. A known method is selected as appropriate for the process for forming the intermediate layer 4 and the process for forming the protective layer.

EXAMPLES

The following describes the present disclosure more specifically using examples. However, the present disclosure is by no means limited to the scope of the examples.

<1. Materials of Photosensitive Member>

As materials for forming a single-layer photosensitive layer of each single-layer photosensitive member, a hole transport material, charge generating materials, and electron transport materials described below were prepared.

<1-1. Electron Transport Material>

Quinone derivatives (1-1), (1-2), (2-1), and (2-2) were produced as the electron transport materials by respective methods described below.

<1-1-1. Production of Quinone Derivative (1-1)>

The quinone derivative (1-1) was produced through reaction (r-1).

(A1-1)

(1-1)

In the reaction (r-1), a phenol derivative (hereinafter may be referred to as a phenol derivative (A1-1)) represented by chemical formula (A1-1) was oxidized to obtain the quinone derivative (1-1). Specifically, a 200-mL flask was used as a reaction vessel. The reaction vessel was charged with 0.95 g (1 mmol) of the phenol derivative (A1-1) and 30 mL of chloroform to prepare a chloroform solution. Further, potassium permanganate (0.79 g, 5 mmol) was added into the reaction vessel. Then, the contents in the reaction vessel were stirred for 12 hours at room temperature (25° C.). Subsequently, the contents in the reaction vessel were filtered to obtain a filtrate. The solvent in the filtrate was evaporated. The filtrate from which the solvent had been evaporated was purified by silica gel column chromatography using chloroform as a developing solvent. Further, recrystallization was performed using chloroform. Through the above, the quinone derivative (1-1) was obtained. An obtained amount of the quinone derivative (1-1) was 0.38 g (percentage yield of 40 mol %).

<1-1-2. Production of Quinone Derivative (1-2)>

The quinone derivative (1-2) was produced by the same procedure as the production of the quinone derivative (1-1) in all aspects other than that the phenol derivative (A1-1) was changed to a phenol derivative (A1-2). Note that each raw material used in the production of the quinone derivative (1-2) was added in the same number of moles as the number of moles of a corresponding raw material used in the production of the quinone derivative (1-1).

Table 1 indicates the phenol derivative (A1) and the quinone derivative (1) in the reaction (r-1). Here, the phenol derivative (A1) is a reactant in the reaction (r-1). Table 1 indicates obtained amounts and percentage yields of the quinone derivative (1).

In Table 1, "1-1" and "1-2" in the column "Type" of the quinone derivative (1) indicate the quinone derivative (1-1) and the quinone derivative (1-2), respectively. Also, "A1-1" and "A1-2" in the column "Type" of the phenol derivative (A1) indicate the phenol derivative (A1-1) and the phenol derivative (A1-2), respectively. The phenol derivative (A1-2) is represented by chemical formula (A1-2).

TABLE 1

| | Reaction (r-1) | | | | |
|---|---|---|---|---|---|
| | Phenol derivative (A1) | | Quinone derivative (1) | | |
| Type | Added amount [g] | Added amount [mmol] | Type | Obtained amount [g] | Percentage yield [mol %] |
| A1-1 | 0.95 | 1 | 1-1 | 0.38 | 40 |
| A1-2 | 0.82 | 1 | 1-2 | 0.37 | 45 |

(A1-2)

<1-1-3. Production of Quinone Derivatives (2-1) and (2-2)>

The quinone derivative (2-1) was produced through reaction (r-2).

(A2-1)

(2-1)

The quinone derivative (2-1) was produced through the reaction (r-2) by the same procedure as the production of the quinone derivative (1-1) in all aspects other than that the phenol derivative (A1-1) in the reaction (r-1) was changed to a phenol derivative (A2-1). The quinone derivative (2-2) was produced by the same procedure as the production of the quinone derivative (1-1) in all aspects other than that the phenol derivative (A1-1) in the reaction (r-1) was changed to a phenol derivative (A2-2). Note that each raw material used in the production of the quinone derivatives (2-1) and (2-2) was added in the same number of moles as the number of moles of a corresponding raw material used in the production of the quinone derivative (1-1). Table 2 indicates obtained amounts and percentage yields of the quinone derivative (2).

In Table 2, "2-1" and "2-2" in the column "Type" of the quinone derivative (2) indicate the quinone derivative (2-1) and the quinone derivative (2-2), respectively. Also, "A2-1" and "A2-2" in the column "Type" of the phenol derivative (A2) indicate the phenol derivative (A2-1) and the phenol derivative (A2-2), respectively. The phenol derivative (A2-2) is represented by chemical formula (A2-2).

TABLE 2

| | Reaction (r-2) | | | | |
|---|---|---|---|---|---|
| | Phenol derivative (A2) | | Quinone derivative (2) | | |
| Type | Added amount [g] | Added amount [mmol] | Type | Obtained amount [g] | Percentage yield [mol %] |
| A2-1 | 0.78 | 1 | 2-1 | 0.39 | 50 |
| A2-2 | 0.71 | 1 | 2-2 | 0.32 | 45 |

(A2-2)

Next, ¹H-NMR spectrums of the produced quinone derivatives (1-1), (1-2), (2-1), and (2-2) were measured using a proton nuclear magnetic resonance spectrometer (product of JASCO Corporation, 300 MHz). CDCl₃ was used as a solvent. Tetramethylsilane (TMS) was used as an internal standard sample. It was confirmed from the ¹H-NMR spectrums that the quinone derivatives (1-1), (1-2), (2-1), and (2-2) were obtained.

<1-1-4. Preparation of Compound (E-1)>

A compound represented by chemical formula (E-1) (hereinafter may be referred to as a compound (E-1)) and a compound represented by chemical formula (E-2) (hereinafter may be referred to as a compound (E-2)) were prepared as the electron transport materials.

<1-2. Hole Transport Material>

The above-described hole transport material (H-1) was prepared as the hole transport material.

<1-3. Charge Generating Material>

The above-described compounds (C-1) and (C-2) were prepared as the charge generating materials. The compound (C-1) was a metal-free phthalocyanine pigment (X-form metal-free phthalocyanine pigment) represented by chemical formula (C-1). The compound (C-1) had an X-form crystal structure.

The compound (C-2) was a titanyl phthalocyanine pigment (Y-form titanyl phthalocyanine pigment) represented by chemical formula (C-2). The compound (C-2) had a Y-form crystal structure. In an X-ray diffraction spectrum of the Y-form titanyl phthalocyanine, presence of a main peak at a Bragg angle (2θ±0.2°) of 27.2° was confirmed.

<1-4. Binder Resin>

A polycarbonate resin (Resin-1) ("PANLITE (registered Japanese trademark) TS-2050", manufactured by Teijin Limited, viscosity average molecular weight: 50,000) described above in the present embodiment was prepared as a binder resin.

<2. Production of Single-Layer Photosensitive Member>

Single-layer photosensitive members (A-1) to (A-8) and (B-1) to (B-4) were produced using the materials for forming the photosensitive layer.

<2-1. Production of Single-Layer Photosensitive Member (A-1)>

A container was charged with 5 parts by mass of the compound (C-1) as the charge generating material, 50 parts by mass of the hole transport material (H-1), 30 parts by mass of the quinone derivative (1-1) as the electron transport material, 100 parts by mass of the polycarbonate resin (Resin-1) as the binder resin, and 800 parts by mass of tetrahydrofuran as a solvent. The contents in the container were mixed for 50 hours using a ball mill to disperse the materials (the compound (C-1), the compound (H-1), the quinone derivative (1-1), and the polycarbonate resin (Resin-1)) in the solvent. Through the above, an application liquid for single-layer photosensitive layer formation was obtained. The application liquid for single-layer photosensitive layer formation was applied onto an aluminum drum-shaped support (diameter: 30 mm, total length: 238.5 mm) as a conductive substrate by dip coating to form an applied film. The applied film was dried using hot air at 100° C. for 60 minutes. Through the above, a single-layer photosensitive layer (film thickness: 30 μm) was formed on the conductive substrate. As a result, the single-layer photosensitive member (A-1) was obtained.

<2-2. Production of Single-Layer Photosensitive Members (A-2) to (A-8) and (B-1) to (B-4)>

The single-layer photosensitive members (A-2) to (A-8) and (B-1) to (B-4) were each produced by the same procedure as the production of the single-layer photosensitive member (A-1) in all aspects other than the following changes. The compound (C-1) used as the charge generating material in the production of the single-layer photosensitive member (A-1) was changed to charge generating materials indicated in Table 3. The quinone derivative (1-1) used as the electron transport material in the production of the single-layer photosensitive member (A-1) was changed to electron transport materials indicated in Table 3. Note that compositions of the photosensitive members (A-1) to (A-8) and (B-1) to (B-4) are indicated in Table 3. In Table 3, CGM, HTM, and ETM indicate the charge generating material, the hole transport material, and the electron transport material, respectively. In Table 3, "x-H₂Pc" and "Y-TiOPc" in the column "CGM" indicate the X-form metal-free phthalocyanine pigment and the Y-form titanyl phthalocyanine pigment, respectively. Further, "H-1" in the column "HTM" indicates the compound (H-1). Further, "1-1", "1-2", "2-1", "2-2", "E-1", and "E-2" in the column "ETM" indicate the quinone derivative (1-1), the quinone derivative (1-2), the quinone derivative (2-1), the quinone derivative (2-2), the compound (E-1), and the compound (E-2), respectively.

<3. Performance Evaluation of Photosensitive Member>

<3-1. Evaluation of Electrical Characteristics of Single-Layer Photosensitive Member>

Electrical characteristics of each of the produced single-layer photosensitive members (A-1) to (A-8) and (B-1) to (B-4) were evaluated. Evaluation of the electrical characteristics was performed in an environment at a temperature of 23° C. and a relative humidity of 60% RH. First, a surface of the single-layer photosensitive member was charged to a positive polarity using a drum sensitivity test device (product of Gen-Tech, Inc.). Charging conditions were set as follows. A rotation speed of the single-layer photosensitive member was set at 31 rpm, and an electric current flowing into the single-layer photosensitive member was set at +8 µA. A surface potential of the single-layer photosensitive member immediately after the charging was set at +700 V. Then, monochromatic light (wavelength: 780 nm, half-width: 20 nm, light intensity: 16 µW/cm$^2$) was obtained from white light emitted from a halogen lamp using a bandpass filter. The surface of the single-layer photosensitive member was irradiated with the obtained monochromatic light (irradiation time: 80 milliseconds). A surface potential of the single-layer photosensitive member was measured when 330 milliseconds elapsed from the start of the irradiation (exposure to the light). The measured surface potential was determined as an electric potential ($V_L$, unit: V) after the exposure to the light. The measured electric potential ($V_L$) of the single-layer photosensitive member after the exposure to the light is indicated in Table 3. Note that a smaller absolute value of the electric potential ($V_L$) after the exposure to the light indicates more excellent electrical characteristics of the single-layer photosensitive member.

TABLE 3

| Photosensitive member No. | Photosensitive layer | | | Electric characteristics |
|---|---|---|---|---|
| | CGM | HTM | ETM | $V_L$(V) |
| Example 1 | A-1 | x-H$_2$Pc | H-1 | 1-1 | +157 |
| Example 2 | A-2 | Y-TiOPc | H-1 | 1-1 | +159 |
| Example 3 | A-3 | x-H$_2$Pc | H-1 | 1-2 | +155 |
| Example 4 | A-4 | Y-TiOPc | H-1 | 1-2 | +157 |
| Example 5 | A-5 | x-H$_2$Pc | H-1 | 2-1 | +162 |
| Example 6 | A-6 | Y-TiOPc | H-1 | 2-1 | +164 |
| Example 7 | A-7 | x-H$_2$Pc | H-1 | 2-2 | +161 |
| Example 8 | A-8 | Y-TiOPc | H-1 | 2-2 | +164 |
| Comparative example 1 | B-1 | x-H$_2$Pc | H-1 | E-1 | +170 |
| Comparative example 2 | B-2 | Y-TiOPc | H-1 | E-1 | +172 |
| Comparative example 3 | B-3 | x-H$_2$Pc | H-1 | E-2 | +177 |
| Comparative example 4 | B-4 | Y-TiOPc | H-1 | E-2 | +180 |

As indicated in Table 3, in each of the photosensitive members (A-1) to (A-8), the photosensitive layer contained any one of the quinone derivatives (1-1), (1-2), (2-1), and (2-2) as the electron transport material. The quinone derivatives (1-1) and (1-2) were represented by general formula (1). The quinone derivatives (2-1) and (2-2) were represented by general formula (2). In each of the photosensitive members (A-1) to (A-8), the electric potential $V_L$ after the exposure to the light was at least +155 V and no greater than +164 V.

As indicated in Table 3, in each of the photosensitive members (B-1) to (B-4), the photosensitive layer contained the compound (E-1) or (E-2) as the electron transport material. The compounds (E-1) and (E-2) were represented by neither of general formula (1) and general formula (2). In each of the photosensitive members (B-1) to (B-4), the electric potential $V_L$ after the exposure to the light was at least +170 V and no greater than +180 V.

It is apparent that the photosensitive members (A-1) to (A-8) are superior to the photosensitive members (B-1) to (B-4) in sensitivity characteristics.

From the above results, it is apparent that the photosensitive member including the photosensitive layer that contains the quinone derivative represented by general formula (1) or (2) is excellent in sensitivity characteristics.

What is claimed is:

1. An electrophotographic photosensitive member comprising a conductive substrate and a photosensitive layer, wherein
the photosensitive layer contains a charge generating material, a hole transport material, a quinone derivative, and a binder resin, and
the quinone derivative is represented by general formula (1) or (2), (1)

(2)

in the general formula (1),
R$^1$, R$^2$, and R$^3$ each represent, independently of one another, a hydrogen atom, an alkyl group having a carbon number of at least 1 and no greater than 12, an aryl group having a carbon number of at least 6 and no greater than 14, an aralkyl group having a carbon number of at least 7 or no greater than 12, or a cycloalkyl group having a carbon number of at least 3 and no greater than 10, the aryl group having a carbon number of at least 6 and no greater than 14 may be substituted with an alkyl group having a carbon number of at least 1 and no greater than 6, in the general formula (2), R⁴ and R⁵ each represent, independently of one another, a hydrogen atom, an alkyl group having a carbon number of at least 1 and no greater than 12, an aryl group having a carbon number of at least 6 and no greater than 14, an aralkyl group having a carbon number of at least 7 and no greater than 12, or a cycloalkyl group having a carbon number of at least 3 and no greater than 10, the aryl group having a carbon number of at least 6 and no greater than 14 may be substituted with an alkyl group having a carbon number of at least 1 and no greater than 6, and Z represents an oxygen atom or a sulfur atom.

2. The electrophotographic photosensitive member according to claim 1, wherein in the general formula (1), R¹, R², and R³ each represent, independently of one another, an alkyl group having a carbon number of at least 1 and no greater than 12 or an aryl group that has a carbon number of at least 6 and no greater than 14 and that is substituted with an alkyl group having a carbon number of at least 1 and no greater than 6, in the general formula (2), R⁴ and R⁵ each represent, independently of one another, an alkyl group having a carbon number of at least 1 and no greater than 12 or an aryl group that has a carbon number of at least 6 and no greater than 14 and that is substituted with an alkyl group having a carbon number of at least 1 and no greater than 6, and

Z represents a sulfur atom.

3. The electrophotographic photosensitive member according to claim 1, wherein the quinone derivative represented by the general formula (1) is represented by chemical formula (1-1) or (1-2), and the quinone derivative represented by the general formula (2) is represented by chemical formula (2-1) or (2-2).

(1-1)

(1-2)

(2-1)

(2-2)

4. The electrophotographic photosensitive member according to claim 1, wherein
   the photosensitive layer is a single-layer photosensitive layer.

5. The electrophotographic photosensitive member according to claim 1, wherein
   the charge generating material is an X-form metal-free phthalocyanine pigment.

6. The electrophotographic photosensitive member according to claim 1, wherein
   the hole transport material is represented by general formula (3), (3)

in the general formula (3), $R^{21}$, $R^{22}$, $R^{23}$, $R^{24}$, $R^{25}$, and $R^{26}$ each represent, independently of one another, an alkyl group having a carbon number of at least 1 and no greater than 6 or an alkoxy group having a carbon number of at least 1 and no greater than 6, p, q, v, and w each represent, independently of one another, an integer from 0 to 5, and m and n each represent, independently of one another, an integer from 0 to 4.

7. The electrophotographic photosensitive member according to claim 6, wherein in the general formula (3), $R^{21}$, $R^{22}$, $R^{23}$, $R^{24}$, $R^{25}$, and $R^{26}$ each represent an alkyl group having a carbon number of at least 1 and no greater than 6, and p, q, v, w, m, and n each represent 1.

* * * * *